United States Patent

Swinney et al.

[11] 4,081,389
[45] Mar. 28, 1978

[54] LUBRICANT COMPOSITION CONTAINING A TRIKETONE

[75] Inventors: Brian Swinney; Roger Scattergood, both of Wantage, England

[73] Assignee: Exxon Research & Engineering Co., Linden, N.J.

[21] Appl. No.: 739,116

[22] Filed: Nov. 5, 1976

[30] Foreign Application Priority Data

Nov. 7, 1975 United Kingdom ............... 46193/75

[51] Int. Cl.² ............................................. C10M 1/20
[52] U.S. Cl. .................................... 252/52 R; 252/73
[58] Field of Search ................... 252/52 R, 73; 208/47

[56] References Cited

U.S. PATENT DOCUMENTS

| 2,315,063 | 3/1943 | Lieber | 252/52 R |
| 3,962,124 | 6/1976 | Motz et al. | 252/52 R |
| 4,018,693 | 4/1977 | Mead et al. | 252/52 R |

FOREIGN PATENT DOCUMENTS

| 633,522 | 12/1961 | Canada | 252/52 R |
| 493,524 | 10/1938 | United Kingdom | 252/52 R |
| 548,038 | 9/1942 | United Kingdom | 252/52 R |

Primary Examiner—Delbert E. Gantz
Assistant Examiner—J. Thierstein
Attorney, Agent, or Firm—Frank T. Johmann

[57] ABSTRACT

A lubricant containing compounds of the general formula:

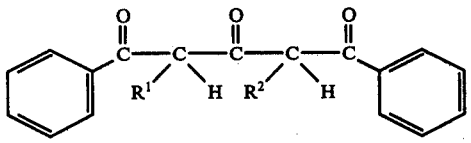

where $R^1$ and $R^2$ are hydrogen or hydrocarbyl.

5 Claims, No Drawings

LUBRICANT COMPOSITION CONTAINING A TRIKETONE

The present invention relates to lubricant compositions and in particular to lubricant compositions having improved anti-rust properties.

In the operation of an internal combustion engine some of the combustion products, including water tend to pass the pistons into the crankcase. When this happens the water in the lubricating oil tends to rust the metal parts. Anti-rust agents are therefore often included in lubricating oils. Most anti-rust agents contain metals and form deposits known as ash when the additives degrade due to the heat generated by the engine. There is therefore a general desire to produce ashless or metal-free additives for lubricating oils and the present invention is concerned with ashless anti-rust additives.

1,3,5 triketones are known compounds but we have now found that certain aromatic triketones are particularly effective as anti-rust additives in lubricating oils.

The present invention therefore provides a lubricating oil containing a minor amount of a compound of the general formula

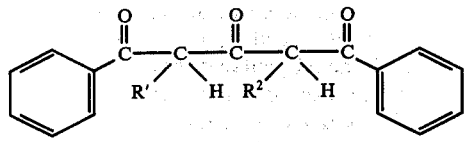

wherein $R^1$ and $R^2$ are hydrogen or hydrocarbyl and may both form part of a cyclic structure.

The aromatic nuclei of the compounds incorporated into the lubricating oil according to our invention may be substituted providing the substituent does not unduly interfere with the anti-rust effect of the compound. For example the oil solubility of the compounds may be improved by the presence of an alkyl substituent of at least six carbon atoms on one or both of the aromatic nucleii.

Triketones themselves are known compounds and various methods may be used for their production. For example the triketone in which $R^1$ and $R^2$ are part of the same cyclohexyl group may be prepared by condensing two moles of methyl benzoate with one mole of cyclohexanone in the presence of a base such as sodium hydride i.e.

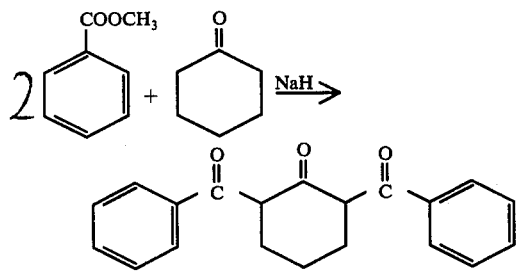

Alternatively the triketones may be prepared by the condensation of acetophenones with ethyl carbonate, again in the presence of a base. In each instance the reaction is preferably carried out under anhydrous conditions in an inert solvent. Triketones with substituents on the aromatic nucleus may be prepared from substituted acetophenones which may themselves be prepared from detergent alkylates.

The lubricant compositions of the present invention may contain other conventional additives such as dispersants, especially the metal free or ashless dispersants of the polyamine long alkyl chain mono or di-carboxylic acid type. Particularly suitable dispersants are the reaction products of polyisobutylene succiniamide and tetra-ethylene pentamine.

Examples of others additives are antioxidants such as the well known zinc dialkyl dithiophosphates, antiwear additives which generally contain sulphur and highly basic metal phenates or sulphonates especially highly basic magnesium or calcium phenates or sulphonates. These highly basic additives are well known and consist of the metal carbonate dispersed in the phenate or the sulphonate.

The method of preparing the lubricant composition will depend upon the nature of the triketone. Some triketones such as 1,5-diphenylpentane-1,3,5-trione are solids and thus special blending techniques are required. Triketones with alkyl substituents in the aromatic nucleus, particularly those where the alkyl group contains more than six carbon atoms, are oil soluble and thus require no special blending techniques.

The triketones have been found to impart good antirust properties to lubricating oils and may therefore be used whenever antirust properties are needed. They may be used in synthetic or natural oils. Examples of synthetic oils include the synthetic ester lubricating oils such as di-octyl adipate, dioctyl sebacate, didecyl azelate, tridecyl adipate, didecyl succinate, didecyl glutarate and mixtures thereof. Alternatively the synthetic ester can be a polyester such as that prepared by reacting polyhydric alcohols such as trimethylol propane and pentaerythritol with monocarboxylic acids such as butyric acid, caproic acid, caprylic acid and pelargonic acid to give the corresponding tri and tetra- esters. Complex esters may also be used such as those formed by esterification reactions between a dicarboxylic acid, a glycol and an alcohol and/or a monocarboxylic acid.

The natural oils may be any animal, vegetable or mineral oil although the present invention is particularly concerned with mineral oils which may be naphthenic or paraffinic. The invention is particularly concerned with crank case lubricants for motor vehicles which may contain from 0.1% to 2.0% by weight of the triketone.

The triketone may be supplied in the form of a concentrate which may optionally contain the other suitable additives. The present invention therefore further provides a concentrate comprising oil and from 1% to 20% by weight of a triketone of the general formula

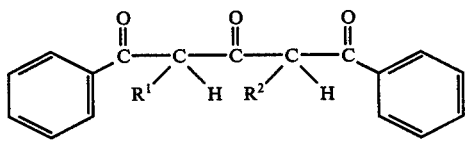

where $R^1$ and $R^2$ may be the same or different and may be hydrogen or hydrocarbyl or may form part of the same ring structure.

The present invention is illustrated but in no way limited by reference to the following examples.

EXAMPLES 1

1,5 diphenyl pentanetrione was prepared by dissolving acetone (11.6g) and methyl benzoate (81.6g) in glyme (150 ml.) and adding this to a slurry of sodium hydride (30g.) in glyme (200 ml.) at reflux temperature after refluxing for six hours the solvent was removed, ether added and the excess sodium hydride destroyed by water. The product was extracted with water and precipitated by addition of concentrated hydrochloric acid.

The product after crystallisation from ethanol was a yellow solid melting at 110° C which could be dissolved in mineral oil at 100° C and when blended with a conventional lubricating oil ashless dispersant was soluble in the mineral oil at 60° C.

An oil containing 0.5% by weight of this diphenyltriketone with 5.5 wt% of a conventional dispersant were subjected to the ASTM D-665 rust test with N/5 hydrochloric acid in which a steel pin is submerged in a sample of oil which is held at 140° F for 24 hrs. The pin remained clean and bright whilst a similar pin submerged in a similar oil without the triketone rusted under the same conditions.

EXAMPLE 2

2:6- dibenzoyl cyclohexanone was prepared by dissolving 80 grams of methyl benzoate and 30.4 mls of cyclohexanone in 50 mls of glyme and adding this to a slurry of 35.2 grams of sodium hydride in 500 mls of glyme and the mixture refluxed for 7 hours. The product was then dissolved in ether, excess sodium hydride reacted with water and the product extracted from the ethereal solution with water and precipitated with hydrochloric acid.

The product was soluble in mineral oil at 100° C and at 60° C when blended with a conventional mineral oil dispersant.

Oils containing 0.5% and 1% by weight of this 2:6 dibenzoyl cyclohexanone with 5.5% by weight of a conventional dispersant were subjected to the same ASTM D-665 test as used in Example 1 and the pin remained clean and bright.

What is claimed is:

1. A lubricating oil containing about 0.1 to 20 wt. % of a triketone of the general formula:

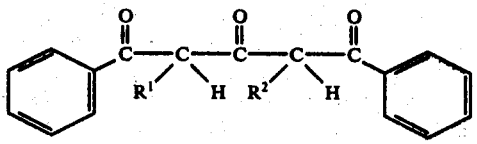

where $R^1$ and $R^2$ are hydrogen or hydrocarbyl.

2. A lubricating oil according to claim 1 in which $R^1$ and $R^2$ both form part of a cyclic structure.

3. A lubricating oil according to claim 2 in which $R^1$ and $R^2$ are part of the same cyclohexyl group.

4. A lubricating oil according to claim 1 wherein said triketone is 1,5-diphenyl pentanetrione.

5. A lubricating oil according to claim 1 wherein said triketone is 2,6-dibenzoyl cyclohexanone.